(12) United States Patent
Hemmilä et al.

(10) Patent No.: US 7,381,567 B2
(45) Date of Patent: Jun. 3, 2008

(54) DISSOCIATIVE FLUORESCENCE ENHANCEMENT ASSAY

(75) Inventors: Ilkka Hemmilä, Kaarina (FI); Kaj Blomberg, Åbo (FI); Veli-Matti Mukkala, Kaarina (FI); Harri Hakala, Turku (FI)

(73) Assignee: Wallac Oy, Turku (FI)

( * ) Notice: Subject to any disclaimer, the term of this patent is extended or adjusted under 35 U.S.C. 154(b) by 0 days.

(21) Appl. No.: 11/516,740

(22) Filed: Sep. 7, 2006

(65) Prior Publication Data

US 2007/0015284 A1    Jan. 18, 2007

Related U.S. Application Data

(62) Division of application No. 10/093,034, filed on Mar. 8, 2002, now Pat. No. 7,211,440.

(51) Int. Cl.
*G01N 33/00* (2006.01)
*G01N 33/53* (2006.01)
*G01N 33/566* (2006.01)
*C12Q 1/68* (2006.01)

(52) U.S. Cl. ............... 436/100; 436/501; 436/800; 436/86; 435/6

(58) Field of Classification Search ............... 436/100
See application file for complete search history.

(56) References Cited

U.S. PATENT DOCUMENTS

| | | | | |
|---|---|---|---|---|
| 4,565,790 A | 1/1986 | Hemmilä et al. | ............ | 436/537 |
| 4,808,541 A | 2/1989 | Mikola et al. | ............ | 436/501 |
| 5,124,268 A | 6/1992 | Dakubu | ............ | 436/537 |
| 5,316,909 A * | 5/1994 | Xu | ............ | 435/6 |
| 5,637,509 A | 6/1997 | Hemmilä et al. | ............ | 436/537 |
| 6,030,840 A * | 2/2000 | Mullinax et al. | ............ | 436/82 |
| 6,127,529 A | 10/2000 | Kwiatkowski et al. | ............ | 534/10 |

(Continued)

FOREIGN PATENT DOCUMENTS

EP    0 064 484    7/1986

(Continued)

OTHER PUBLICATIONS

Soukka et al., Supersensitive Time-resolved Immunofluorometric Assay of Free Prostate-specific Antigen with Nanoparticle Label Technology, 2001, Clinical Chemistry, vol. 47(7), pp. 1269-1278.*

(Continued)

*Primary Examiner*—Jill Warden
*Assistant Examiner*—Lore Ramillano
(74) *Attorney, Agent, or Firm*—James C. Lydon

(57) ABSTRACT

The invention relates to an enhancement solution for an assay technology using lanthanide ions or their chelates as labels and dissociative fluorescence enhancement as a tool for detection, wherein said enhancement solution comprises a β-diketone of formula I $$R_1 - \underset{\underset{O}{\|}}{C} - CH_2 - \underset{\underset{O}{\|}}{C} - R_2 \qquad (I)$$

wherein $R_1$ is an aryl, optionally mono- or multi-substituted, and $R_2$ is a straight or branched alkyl chain with 2 to 9 carbon atoms substituted with four or more fluorine atoms. The invention further relates to a bioaffinity assay using lanthanide ions or their chelates as labels and dissociative fluorescence enhancement as a tool for detection comprising the use of said enhancement solution.

9 Claims, 2 Drawing Sheets

U.S. PATENT DOCUMENTS

| | | | |
|---|---|---|---|
| 6,329,205 B1 * | 12/2001 | Diwu et al. | 436/86 |
| 6,429,026 B1 * | 8/2002 | Pettersson et al. | 436/518 |
| 2002/0106674 A1 * | 8/2002 | Matsui et al. | 435/6 |

FOREIGN PATENT DOCUMENTS

| | | |
|---|---|---|
| EP | 0 139 675 | 1/1987 |
| EP | 0324 323 | 7/1989 |
| EP | 0 298 939 | 1/1994 |
| WO | WO 89/04375 | 5/1989 |
| WO | WO 98/15830 | 6/1997 |
| WO | WO 99/66333 | 12/1999 |
| WO | WO 03/033447 | 4/2003 |

OTHER PUBLICATIONS

Hemmilá et al., "Time-Resolution in Fluorometry Technologies, Labels, and Applications in Bioanalytical Assays," 441 *Critical Reviews in Clinical Laboratory Sciences* 441-519 (2001).

Pettersson et al., "Time-resolved Fluorometry (TRF)-based Immunoassay Concept For Rapid and Quantitative Determination of Biochemical Myocardial Infarction Markers From Whole Blood, Serum and Plasma," 399 *Luminescence* 399-407 (2000).

Hemmilä et al., *Bioanalytical Applications of Labelling Technologies* 1-394 (Wallac 1994).

Hemmilä et al., *Applications of Fluorescence In Immunoassays*, 1-248 (J. Wiley & Sons, Inc. 1991).

Hemmilä et al., Di- and tetracarboxylate derivatives of pyridines, bipyridines and terpyridines as luminogenic reagents for time-resolved fluorometric determination of terbium and dysprosium, 26 *J.Biochim. and Biophysical Methods* 283 (1993).

Markela et al., "Europium-labelled recombinant protein G—A fast and sensitive universal immunoreagent for time-resolved immunofluorometry," 161 *J. Immunological Methods* 1 (1993).

Joshi, "Studies in Fluorinated 1,3-Diketones and Related Compounds," 47 *J. Fluorine Chem.* 1-11 (1990).

Joshi, "Studies in Fluorinated Beta-Diketones and Related Compounds," 39 *J. Inorg. Nucl. Chem.* 803-810 (1977).

Dilli, "Spectroscopic Properties and Gas Chromatographic Behavior of Aryl Beta-Diketones and Selected Chelates," 312 *J. Chromatography* 109-120 (1984).

* cited by examiner

DISSOCIATIVE FLUORESCENCE ENHANCEMENT ASSAY

This application is a division of U.S. patent application Ser. No. 10/093,034, filed Mar. 8, 2002, now U.S. Pat. No. 7,211,440.

FIELD OF INVENTION

This invention relates to a modification to improve an assay technology commercially known as DELFIA®, which uses lanthanide ions or their chelates as labels and dissociative fluorescence enhancement as a tool for detection.

BACKGROUND OF THE INVENTION

The publications and other materials used herein to illuminate the background of the invention and, in particular, cases to provide additional details respecting the practice, are incorporated by reference.

Lanthanides and their chelates have become an important group of labels in various assays, such as immunoassays, hybridization assays, receptor-ligand assays and others [reviews: Hemmilä, Application of Fluorescence in Immunoassays, Wiley, 1991; Hemmilä, Ståhlberg and Mottram (eds.), Bioanalytical Applications of Labeling Technologies, Wallac, 1995; Hemmilä and Mukkala, Crit. Rev. Clin. Lab. Sci., 38(6): 441-519 (2001)]. The long excited state lifetimes of lanthanides makes it possible to exploit very efficiently and simply time-resolution in order to get rid of background interferences and to obtain ultimate sensitivities of fluorometry. Other advantages of lanthanide labels relate to their exceptional spectral properties such as long Stokes' shifts (over 250 nm) and narrow banded ion-characteristic emission lines. The spectral properties allow lanthanides to be used in real multi-label assays where the detection can take advantage of both spectral and temporal resolutions.

There are numerous technologies using lanthanides as labels. The first and the original technology, i.e. the DELFIA® technology, uses two chelate systems, one optimized for labeling and the second, which is created after the actual assay is accomplished, to enable fluorescence enhancement and detection (U.S. Pat. No. 4,565,790, EP 0 064 484). This technology is still the most sensitive and widely used. It has many applications in diagnostics, screening, drug discovery and other research areas. Regardless of an extensive search and numerous patents, development of a single lanthanide chelate structure with optimized properties allowing similar assay performances without enhancement has remained a challenge, due to e.g. energy transfer, intensity, protection, biocompatibility and coupling problems.

A major problem with the original DELFIA® technology relates to the change in ligand of the enhancement process. Using existing enhancement composed of trifluoro derivatives of β-diketones, most commonly naphthoyltrifluoroacetone (β-NTA, i.e. 4,4,4-trifluoro-1-(2-naphthyl)-1,3-butanedione), the lowest pH one can use is about 3.0. A special protein labeling chelate for that purpose has therefore been developed based on diethylenetriamine-N,N',N'',N'''-tetraacetate group (DTTA) (U.S. Pat. No. 4,808,541, EP 0 139 675), which at the pH applied in the enhancement solution rapidly releases europium ions and creates new, highly fluorescent chelates with naphthoyltrifluoroacetone present in excess in the enhancement solution.

When a bioassay requires a labeling chelate of higher thermodynamic or kinetic stability, the original enhancement system requires considerably longer time for enhancement, which is not convenient or even acceptable when rapid universal systems are to be developed. For example, the use of DNA probes quite often require a more stable labeling chelate reagent and for DNA based applications lanthanide chelate of 2,2',2'',2'''-[[4-[2-(4-isothiocyanatophenyl)ethyl]-pyridine-2,6-diyl]bis(methylenenitrilo)]tetrakis(acetic acid) (EP 0 298 939, U.S. Pat. No. 6,127,529) is found optimal. The chelate used, however, requires longer fluorescence development times and routinely 20-30 minutes are required to stabilize the fluorescence in the enhancement solution.

An application where the present DELFIA® technology has been found unsuitable is rapid random access analysis of samples performed with all-in-one dry reagent system [Pettersson et al., Luminescence, 15: 399-407 (2000)]. In this system the drying procedure used to prepare dry-reagent assay-specific all-in-one wells requires a strong chelating reagent due to risk of ion dissociation during the drying process. Use of DTTA chelates optimized for DELFIA® have not been found very suitable for this approach. On the other hand, when more strongly chelating labeling reagents are used, the time required for enhancement becomes too long for the whole process.

Another case where original DELFIA® technology is not suitable is the analysis of plasma samples that may contain high concentration of citrate or EDTA. In one-step assays of analytes (required e.g. in competitive analysis of haptenic antigens) the DELFIA-optimized DTTA chelate can not be used due to the competing chelation processes.

Yet another assay-type requiring improved enhancement/labeling system relates to applications where either free or complexed lanthanides are used as labels. Example of these assays is e.g. cytotoxicity assays, where europium chelate of DTPA is used as intracellular label. Other resembling assays can use lanthanide as labels/tracers for a wide variety of processes (environmental samples, metabolic routes etc.).

A further assay-type requiring label chelates with higher stability than that of DTTA and improved enhancement relates to applications where the reaction mixture contains high concentrations of metal ions. Examples of these assays are e.g. enzyme activity measurements and soil analysis with immunoassays where relatively high amounts of heavy metals may be present.

Mullinax et al. (U.S. Pat. No. 6,030,840, WO 99/66333) modified the DELFIA® method by adding some polyanionic compound to the enhancement solution. They teach that the dissociation of the lanthanide ion from the chelate is faster already at higher pH. The chelates used in their examples are a benzyl-EDTA derivative and DTPA where one acetate group is used for coupling to the biomolecule. The stabilities of these chelates are lower or about the same than those of the DTTA derivative used in the DELFIA® method. There is no proof or data that the method presented by Mullinax et al. would work with more stable chelates used for labeling of biomolecules. Compared to the commercialised enhancement solution (Wallac product), the above mentioned method does not provide improvement, also because the commercial DELFIA® enhancement already contains polyanions (phthalic acid).

Dakubu (U.S. Pat. No. 5,124,268) divided the fluorescence enhancement in two parts. The first part is the dissociation of the metal from the stable lanthanide chelate by lowering the pH to 1.5-3.0. The second part of the process is the change of the pH to over 3.5 and the development of the fluorescent lanthanide chelate. This two-step method is, however, too laborious to be used in automatic diagnostic systems because it demands one extra incubation and addition step.

OBJECT AND SUMMARY OF THE INVENTION

One object of the present invention is to provide a improved enhancement solution for an assay technology using lanthanide ions or their chelates as labels and dissociative fluorescence enhancement as a tool for detection.

Another object of the present invention is to provide an improved assay using lanthanide ions or their chelates as labels and dissociative fluorescence enhancement as a tool for detection.

Thus this invention provides an enhancement solution for an assay technology using lanthanide ions or their chelates as labels and dissociative fluorescence enhancement as a tool for detection, wherein said enhancement solution comprises a β-diketone of formula I

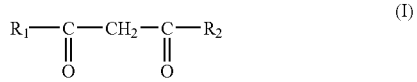

wherein $R_1$ is an aryl, optionally mono- or multi-substituted, and $R_2$ is a straight or branched alkyl chain with 2 to 9 carbon atoms substituted with four or more fluorine atoms optionally mono- or multi-substituted with other substituents than fluorine.

This invention further provides a bioaffinity assay using lanthanide ions or their chelates as labels and dissociative fluorescence enhancement as a tool for detection comprising the steps of a) mixing a sample comprising an analyte to be assayed with reactants of said assay to obtain an assay mixture;

b) reacting said analyte with said reactants, wherein a bio-affinity reaction between said analyte and said reactants of said assay takes place, resulting in a reaction product wherein
  i) the analyte is attached to at least one reactant covalently or noncovalently labeled with a lanthanide or lanthanide chelate, or
  ii) an analyte analogue or other reactant correlating in amount directly or inversely with the analyte, is directly labeled with the lanthanide, wherein the lanthanides of i) and ii) above are herinafter referred to as label lanthanides;

c) separating said reaction product obtained in step b), said product comprising said label lanthanides defined above, from the unbound free labeled reactants;

d) adding the enhancement solution defined above to
  i) dissociate the label lanthanides from the chelates of the reaction products of step b) and
  ii) create a highly fluorescent lanthanide chelate with the β-diketone of said enhancement solution, and e) measuring the amount, directly or inversely correlating with the amount of analyte of the sample in step a), of the label lanthanides of step d) as β-diketone complexes by fluorometry.

DETAILED DESCRIPTION OF THE INVENTION

Figure 1:
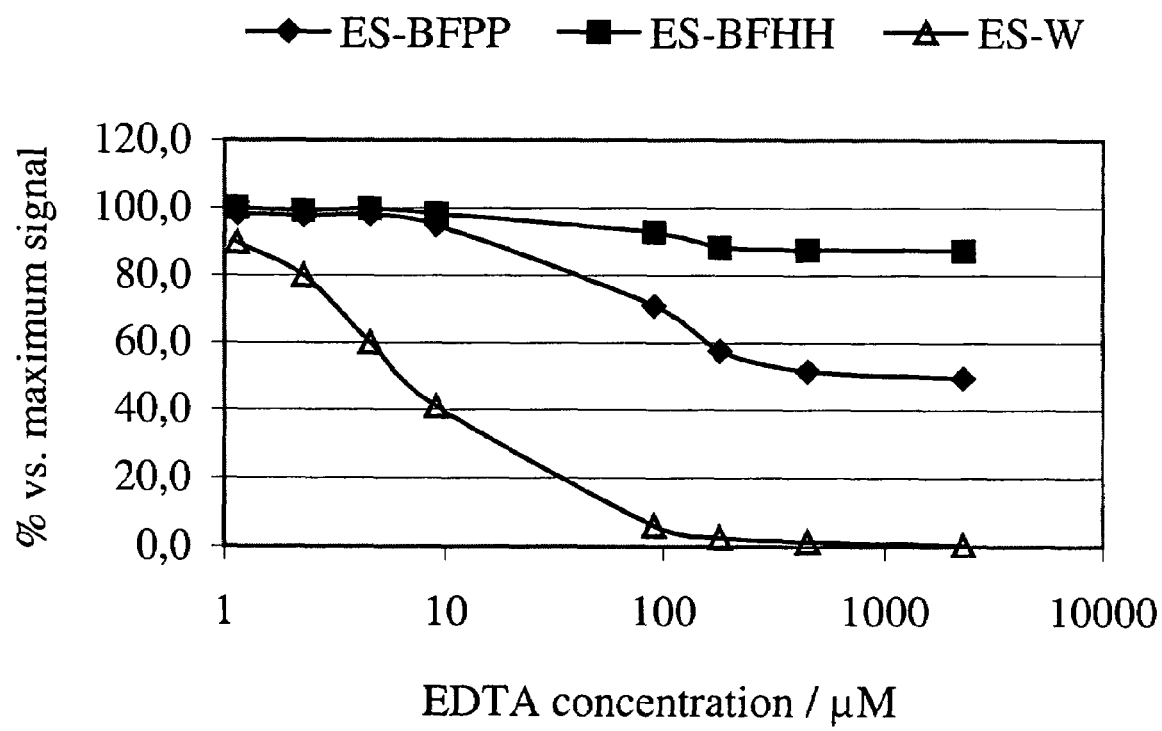
FIG. 1 shows the influence of EDTA concentrations on the lanthanide signals of the enhancement solutions after shaking for one hour.

The present invention relates to an assay technology using lanthanide ions or their chelates as labels and dissociative fluorescence enhancement as a tool for detection. That technology, widely applied in diagnostics and research, is commercially known as DELFIA® technology. The invention provides an improvement to the DELFIA® enhancement process that makes it possible to use a single labeling reagent for all applications and allows a rapid enhancement process even with very stable labeling chelates. The improved enhancement system avoids all the problems mentioned above, and enables rapid ligand exchange kinetics regardless of the application.

By modifying the enhancement process as described here, improvements in speed and robustness are achieved. The new improved enhancement process allows applications requiring more stable label chelates and practically enables the use of a single type of chelate label for all applications. The new enhancement system avoids also the difficulties in the original technology related to e.g. plasma samples and other samples containing high concentrations of EDTA or citrate or other strongly chelating agents, samples and buffers containing high concentration of metal ions, or any assay which for other reasons sets high demands on label chelate stability.

The present invention is made possible by changing the structure of the used β-diketone. β-Diketones have been used as fluorescence enhancing ligands after the dissociation of the metal from the lanthanide chelate used for the labeling of biomolecules. The present enhancement solutions, the one commercialized by Wallac and those described in the literature, are based on trifluoro substituted β-diketones, such as 4,4,4-trifluoro-1-(2-naphthyl)-1,3-butanedione or 4,4,4-trifluoro-1-(2-thienyl)-1,3-butanedione. These compounds are capable of forming luminescent lanthanide chelates at the used dissociation pH of 3.0 to 3.5. If the pH is lower, the trifluorinated β-diketones are not effective any more. According to the present invention, the trifluoromethyl group in the β-diketones is substituted with more highly fluorinated groups hence allowing the use of a lower pH. Preferable β-diketones of the present invention are 1-aryl-4,4,5,5,5-pentafluoro-1,3-pentanedione and 1-aryl-4,4,5,5,6,6,6-heptafluoro-1,3-hexanedione.

The addition of strongly electronegative fluorine atoms in the structure of β-diketones increases their acidity. Due to this effect these new β-diketones are capable of chelating lanthanide metals down to a pH of 2.0 to 2.8. The enhancement solution of this present invention containing these new β-diketones and lower pH speeds up the dissociation rate and new chelate formation. When the dissociation is faster more stable lanthanide chelates can be used for the labeling of biomolecules.

β-Diketones of the structure 4,4,5,5,5-pentafluoro-1-aryl-1,3-pentanedione and 4,4,5,5,6,6,6-heptafluoro-1-aryl-1,3-hexanedione are known in the litterature. Examples, with CA registry numbers in brackets, are 4,4,5,5,5-pentafluoro-1-(3-fluoro-4-methoxyphenyl)-1,3-pentanedione [81516-12-3], 1-(2,5-difluoro-phenyl)-4,4,5,5,5-pentafluoro-1,3-pentanedione [64287-16-7], 4,4,5,5,5-penta-fluoro-1-(4-fluorophenyl)-1,3-pentanedione [64287-12-3], 1-(4-bromophenyl)-4,4,5,5,6,6,6-heptafluoro-1,3-hexanedione [307531-56-2], 1-(9H-fluoren-2-yl)-4,4,5,5,6,6,6-heptafluoro-1,3-hexanedione [202460-66-0] and 1-[1,1'-bi-phenyl]-4-yl-4,4,5,5,6,6,6-heptafluoro-1,3-hexanedione [171666-86-7]), but their use in an assay system has not been described nor suggested.

Thus the present invention concerns an enhancement solution for an assay technology using lanthanide ions or their chelates as labels and dissociative fluorescence enhancement as a tool for detection, wherein said enhancement solution comprises a β-diketone of formula I

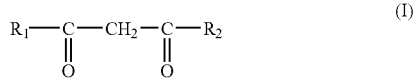

wherein
$R_1$ is an aryl, optionally mono- or multi-substituted, and
$R_2$ is a straight or branched alkyl chain with 2 to 9, preferably 2 to 5, carbon atoms substituted with four or more fluorine atoms optionally mono- or multi-substituted with other substituents than fluorine.

Said aryl of $R_1$ is preferably selected from the group consisting of phenyl, 9H-fluoren-2-yl, 1-naphthyl, 2-naphtyl, 2-phenanthrolyl, 3-phenanthrolyl, 4-phenanthrolyl, 5-phenanthrolyl, 2-furyl, 3-furyl, 2-benzofuryl, 3-benzofuryl, 2-thienyl, 3-thienyl, 2-pyridyl, 3-pyridyl, 4-pyridyl, 2-thiazolyl, 4-thiazolyl, 5-thiazolyl, 2-benzothiazolyl, 2-benzo[b]thienyl, 3-benzo[b]thienyl, 2-pyrimidyl, 4-pyrimidyl and 5-pyrimidyl.

Said aryl of $R_1$ can be mono- or multi-substituted. Each substituent can independently be e.g. a straight or branched alkyl, alkoxy, aryl, aroyl, aryloxy, nitro, amino, cyano, hydroxy, carboxy, chloro, bromo, fluoro or acyl. If the substitutions comprise atoms that can be substituted these can in turn be substituted.

The alkyl chain $R_2$ is preferably substituted with 4 to 9 fluorine atoms and most preferably with 5 to 7 fluorine atoms.

The carbon atoms closest to the carbonyl groups, preferably the first 2 to 5 carbon atoms, of the alkyl chain $R_2$ are substituted with fluorine atoms, preferably 5 to 7 fluorine atoms.

4,4,5,5,5-pentafluoro-1-aryl-1,3-pentanedione or 4,4,5,5,6,6,6-heptafluoro-1-aryl-1,3-hexanedione are preferrable alternatives for β-diketone of the enhancement solution. Typical β-diketones of the enhancement solution are 1-(2-benzofuryl)-4,4,5,5,5-pentafluoro-1,3-pentanedione, 1-(2-benzofuryl)-4,-4,5,5,6,6,6-heptafluoro-1,3-hexanedione, 1-(2-benzo[b]thienyl)-4,4,5,5,5-pentafluoro-1,3-pentanedione and 1-(2-benzo[b]thienyl)-4,4,5,5,6,6,6-heptafluoro-1,3-hexanedione.

$R_2$ can be mono- or multi-substituted with other substituents than fluorine and each substituent can independently be selected from the group consisting of straight or branched alkyl, alkoxy, aryl, aroyl, aryloxy, nitro, amino, cyano, hydroxy, carboxy, chloro, bromo and acyl. If the substitutions comprise atoms that can be substituted these can in turn be substituted.

The enhancement solution is preferably a buffer having a pH of 2.0 to 2.8. The enhancement solution is a preferably a 1 to 50 μM β-diketone solution.

The enhancement solution preferably comprises a detergent that is an alkyl aryl polyether alcohol, zwitterionic, or a quaternary ammonium compound. The enhancement solution typically comprises 0.1% to 0.5% of an alkyl aryl polyether alcohol. Typical alternatives for detergents of the enhancement solution are Triton X-100, 3-[(3-cholamidopropyl)dimethylammonio]-1-propanesulfonate and cetyltrimethylammonium bromide. The enhancement solution preferably comprises a Lewis base that is trialkylphosphine oxide or triarylphosphine oxide. The Lewis base is typically trioctylphosphineoxide and the enhancement solution is preferably a 10 to 100 μM trioctylphosphineoxide solution.

The present invention further concerns a bioaffinity assay using lanthanide ions or their chelates as labels and dissociative fluorescence enhancement as a tool for detection comprising the steps of
a) mixing a sample comprising an analyte to be assayed with reactants of said assay to obtain an assay mixture;
b) reacting said analyte with said reactants, wherein a bio-affinity reaction between said analyte and said reactants of said assay takes place, resulting in a reaction product wherein
  i) the analyte is attached to at least one reactant covalently or noncovalently labeled with a lanthanide or lanthanide chelate, or
  ii) an analyte analogue or other reactant correlating in amount directly or inversely with the analyte, is directly labeled with the lanthanide, wherein the lanthanides of i) and ii) above are herinafter referred to as label lanthanides;
c) separating said reaction product obtained in step b), said product comprising said label lanthanides defined above, from the unbound free labeled reactants preferably using a solid-phase immobilized reactant as catcher;
d) adding the enhancement solution according to the invention to
  i) dissociate the label lanthanides from the chelates of the reaction products of step b) and
  ii) create a highly fluorescent lanthanide chelate with the β-diketone of said enhancement solution, and
e) measuring the amount, directly or inversely correlating with the amount of analyte of the sample in step a), of the label lanthanides of step d) as β-diketone complexes by fluorometry preferably using time-resolution.

Reactants of said assay can comprise a biological binding reagent such as a monoclonal, polyclonal, engineered or fragment antibody, receptor, ligand, natural binding protein, enzyme, peptide, lectin, streptavidin or avidin, oligonucleotide, polynucleotide, binding plastic imprints a cell, cell fragment, membrane or micelle. If the biological binding reagent is a oligonucleotide or polynucleotide said reagent can be selected from the group consisting of DNA, RNA, cDNA, cDNA array, mRNA, PNA or aptamer.

The analyte can be a hapten, antigen, hormone, protein, peptide, drug, virus, DNA sequence, RNA, microbe, environmental toxin, cell, cell fragment, membrane or micelle.

The reaction product of step b) can for example be an immunocomplex, protein-protein complex, antigen-antibody complex, nucleotide hybrid, enzymatic end product or end product of a cellular reaction.

The lanthanide can be europium, terbium, samarium or dysprosium.

A reactant used to measure the analyte can for example be a enzyme substrate.

The method according to the invention can also comprise two or more bioaffinity assays carried out using the same sample and assay mixture by labeling the reactants of each assay with a different lanthanide. The fluorescence of the different lanthanides can be measured using the same enhancement solution.

The invention will now be illustrated by way of the synthesis of suitable β-diketones disclosed in examples 1 to 10. The influence of EDTA concentration on the lanthanide signals of the enhancement solutions is presented in example 11. Example 12 shows the development time of fluorescence in the enhancement solution containing different amounts of 1-(2-benzofuryl)-4,4,5,5,5-pentafluoro-1,3-pentanedione (BFPP) and anti-HCG labeled with europium chelate of (S)-1-(4-isothiocyanatobenzyl)diethylenetriamine-N,N,N',N'',N''-pentaacetic acid.

EXAMPLE 1

4,4,5,5,5-Pentafluoro-1-(2-thienyl)-1,3-pentanedione

2-Acetylthiophene (4.3 ml) was dissolved in dry toluene (40 ml). Sodium hydride (60%, 3.2 g) was added slowly and the mixture was stirred for 15 minutes. Ethyl pentafluoropropionate (13.44 g) was added and the stirring was continued overnight. Sulfuric acid (10%, 50 ml) was added and the phases were separated. The organic phase was washed with water (50 ml) and it was evaporated to dryness. The residue was distilled (b.p. 92-94° C./0.15 mbar) to give the product (9.0 g). $^1$H NMR (CDCl$_3$): 6.50 (s, 1 H); 7.21 (dd, 1H, J=3.9 & 4.9); 7.77 (dd, 1H, J=1.1 & 4.9 Hz); 7.85 (dd, 1H, J=1.1 & 3.9 Hz). IR (film): 1592 (C=O); 1202 (C—F).

EXAMPLE 2

4,4,5,5,6,6,6-Heptafluoro-1-(2-thienyl)-1,3-hexanedione

The compound was synthesized according to example 1 using 2-acetylthiophene and ethyl heptafluorobutyrate as starting materials. $^1$H NMR (CDCl$_3$): 6.49 (s, 1 H); 7.21 (dd, 1H, J=3.8 & 5.1); 7.77 (dd, 1H, J=1.2 & 5.1 Hz); 7.85 (dd, 1H, J=1.2 & 3.8 Hz). IR (film): 1589 (C=O); 1230 (C—F).

EXAMPLE 3

1-(5-Cyano-2-thienyl)-4,4,5,5,5-pentafluoro-1,3-pentanedione

The compound was synthesized according to example 1 using 2-acetyl-5-cyanothiazole and ethyl pentafluoropropionate as starting materials. The product was purified using flash chromatography (silica, 10% ethyl acetate in petroleum ether as an eluent). $^1$H NMR (CDCl$_3$): 6.53 (s, 1 H); 7.68 (d, 1H, J=4.2 Hz); 7.79 (d, 1H, J=4.2 Hz).

EXAMPLE 4

1-(5-Carboxy-2-thienyl)-4,4,5,5,5-pentafluoro-1,3-pentanedione

A mixture of 1-(5-cyano-2-thienyl)-4,4,5,5,5-pentafluoro-1,3-pentanedione (0.78 g), sulfuric acid (9 ml) and acetic acid (10 ml) was refluxed for 2 hours. The cooled mixture was poured into 100 ml of water. The precipitation was filtered and washed with water. $^1$H NMR (CDCl$_3$): 6.53 (s, 1 H); 7.57 (d, 1H, J=4.1 Hz); 7.78 (d, 1H, J=4.1 Hz).

EXAMPLE 5

4,4,5,5,6,6,6-Heptafluoro-1-(2-furyl)-1,3-hexanedione

The compound was synthesized according to example 1 using 2-acetylfuran and ethyl heptafluorobutyrate as starting materials. $^1$H NMR (CDCl$_3$): 6.54 (s, 1 H); 6.65 (dd, 1H, J=1.6 & 3.6 Hz); 7.37 (dd, 1H, J=0.6 & 3.6 Hz); 7.70 (dd, 1H, J=0.6 & 1.6 Hz). IR (film): 1616 (C=O); 1231 (C—F).

EXAMPLE 6

4,4,5,5,5-Pentafluoro-1-(2-naphthyl)-1,3-pentanedione

The compound was synthesized according to example 1 using 2-acetylnaphthalene and ethyl pentafluoropropionate as starting materials. The product was crystallized from petroleum ether. $^1$H NMR (CDCl$_3$): 6.79 (s, 1 H); 7.57-7.67 (m, 2H); 7.90 (bd, 1 H); 7.94-7.95 (m, 2H); 7.99 (bd, 1H); 8.53 (s, 1 H). IR (film): 1602 (C=O); 1201 (C—F).

EXAMPLE 7

4,4,5,5,6,6,6-Heptafluoro-1-(2-naphthyl)-1,3-hexanedione

The compound was synthesized according to example 1 using 2-acetylnaphthalene and ethyl heptafluorobutyrate as starting materials. The product was crystallized from petroleum ether. $^1$H NMR (CDCl$_3$): 6.76 (s, 1 H); 7.57-7.66 (m, 2H); 7.90 (bd, 1 H); 7.93-7.94 (m, 2H); 7.98 (bd, 1 H); 8.53 (s, 1H). IR (film): 1602 (C=O); 1232 (C—F).

EXAMPLE 8

1-(2-Benzo[b]thienyl)-4,4,5,5,5-pentafluoro-1,3-pentanedione

The compound was synthesized according to example 1 using 2-acetylbenzo[b]thienyl and ethyl pentafluoropropionate as starting materials. The product was crystallized from ethanol. $^1$H NMR (CDCl$_3$): 6.63 (s, 1 H); 7.89-7.93 (m, 3 H); 8.12 (d, 1H, J=0.6 Hz). IR (film): 1589 (C=O); 1203 (C—F).

EXAMPLE 9

1-(2-Benzofuryl)-4,4,5,5,5-pentafluoro-1,3-pentanedione

The compound was synthesized according to example 1 using 2-acetylbenzofuran and ethyl pentafluoropropionate as starting materials. The product was crystallized from petroleum ether. $^1$H NMR (CDCl$_3$): 6.75 (s, 1 H); 7.35 (ddd, 1H, J=0.9 & 7.1 & 7.9 Hz); 7.51 (ddd, 1H, J=1.3 & 7.1 & 8.4 Hz); 7.58-7.60 (m, 1 H); 7.67 (d, 1H, J=0.9 Hz); 7.71-7.73 (m, 1 H). IR (film): 1614 (C=O); 1211, 1200 (C—F).

EXAMPLE 10

1-(2-Benzofuryl)-4,4,5,5,6,6,6-heptafluoro-1,3-hexanedione

The compound was synthesized according to example 1 using 2-acetylbenzofuran and ethyl heptafluorobutyrate as starting materials. The product was crystallized from petroleum ether. $^1$H NMR (CDCl$_3$): 6.74 (s, 1 H); 7.35 (ddd, 1H, J=0.9 & 7.2 & 8.0 Hz); 7.52 (ddd, 1H, J=1.3 & 7.2 & 8.4 Hz); 7.58-7.61 (m, 1 H); 7.68 (d, 1H, J=0.9 Hz); 7.71-7.74 (m, 1 H). IR (film): 1614 (C=O); 1232 (C—F).

EXAMPLE 11

The influence of EDTA concentrations on the lanthanide signals of the enhancement solutions after shaking for one hour is presented in FIG. 1. ES-W corresponds to the enhancement solution commercialized by Wallac, ES-BFPP and ES-BFHH are the enhancement solutions of the present invention containing 1-(2-benzofuryl)-4,4,5,5,5-pentafluoro-1,3-pentanedione (BFPP) and 1-(2-benzofuryl)-4,4,5,5,6,6,6-heptafluoro-1,3-hexanedione (BFHH), correspondingly. The contents of the new enhancement solutions are the following: 5 µM β-diketone, 0.2% Triton X-100, 50 µM trioctylphosphine oxide and glycine-HCl-buffer, pH=2, 3.

EXAMPLE 12

Figure 2:
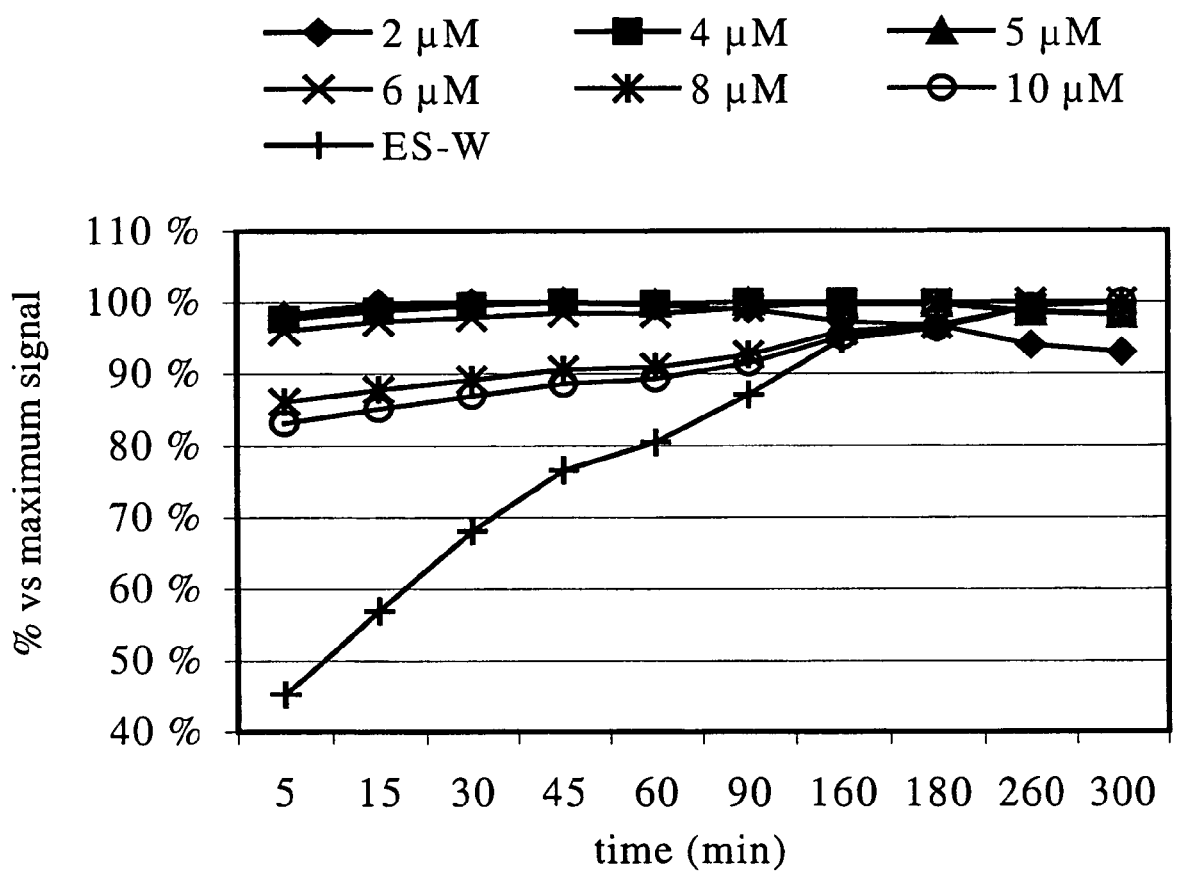
FIG. 2 shows the development time of the fluorescence in the enhancement solution containing different amounts of 1-(2-benzofuryl)-4,4,5,5,5-pentafluoro-1,3-pentanedione (BFPP) and anti-HCG antibody labeled with europium chelate of (S)-1-(4-isothiocyanatobenzyl)diethylenetriamine-N,N,N',N'',N''-pentaacetic acid.

The development time of the fluorescence in the enhancement solution containing different amounts of 1-(2-benzofuryl)-4,4,5,5,5-pentafluoro-1,3-pentanedione (BFPP) and anti-HCG antibody labeled with europium chelate of (S)-1-(4-isothiocyanatobenzyl)diethylenetriamine-N,N,N',N'',N''-pentaacetic acid is presented in FIG. 2. ES-W corresponds to the enhancement solution commercialized by Wallac.

It will be appreciated that the present invention can be incorporated in the form of a variety of embodiments, only a few of which are disclosed herein. It will be apparent for the specialist in the field that other embodiments exist and do not depart from the spirit of the invention. Thus, the described embodiments are illustrative and should not be construed as restrictive.

The invention claimed is:

1. A bioaffinity assay using lanthanide ions or their chelates as labels and dissociative fluorescence enhancement as a tool for detection comprising the steps of
   a) mixing a sample comprising an analyte to be assayed with reactants of said assay to obtain an assay mixture;
   b) reacting said analyte with said reactants, wherein a bioaffinity reaction between said analyte and said reactants of said assay takes place, resulting in a reaction product wherein
      i) the analyte is attached to at least one reactant covalently or noncovalently labelled with a lanthanide or lanthanide chelate, or
      ii) an analyte analogue or other reactant, correlating in amount directly or inversely with the analyte, is directly labeled with the lanthanide,
   wherein the lanthanides of i) and ii) above are hereinafter referred to as label lanthanides,
   c) separating said reaction product obtained in step b), said reaction product comprising said label lanthanides defined above, from the unbound free labeled reactants,
   d) performing a dissociative fluorescence enhancement which consists essentially of adding an enhancement solution having a pH of from 2.0 to 2.8 to
      i) dissociate the label lanthanides from the chelates of the reaction product of step b) and
      ii) create a highly fluorescent lanthanide chelate with a β-diketone of said enhancement solution, said dissociative fluorescence enhancement being performed in a single step, and
   e) measuring the amount, directly or inversely correlating with the amount of analyte of the sample in step a) of the label lanthanides of step d) as β-diketone complexes by fluorometry,
   wherein said enhancement solution comprises a β-diketone of formula I

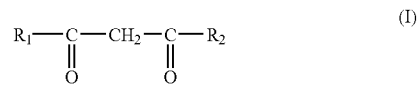

wherein
   R$_1$ is an aryl, optionally mono- or multi-substituted, and R$_2$ is a straight or branched alkyl chain with 2 to 9 carbon atoms substituted with four or more fluorine atoms optionally mono- or multi-substituted with other substituents than fluorine.

2. The method according to claim 1 wherein the separation step c) is carried out using a solid-phase immobilized reactant as catcher.

3. The method according to claim 1 wherein the measuring of step e) is carried out using time-resolution.

4. The method according to claim 1 wherein the assay reactants comprises a biological binding reactant selected from the group consisting of a monoclonal, polyclonal, engineered or fragment antibody, a receptor, ligand, natural binding protein, enzyme, peptide, lectin, streptavidin or avidin, oligonucleotide, polynucleotide, binding plastic imprint, a cell, cell fragment, membrane and micelle.

5. The method according to claim 4 wherein the biological binding reagent is oligonucleotide or polynucleotide selected from the group consisting of DNA, RNA cDNA, cDNA array, mRNA, PNA or aptamer.

6. The method according to claim 1 wherein the analyte is selected from the group consisting of a hapten, antigen, hormone, protein, peptide, drug, virus, DNA sequence, RNA, microbe, environmental toxin, cell, cell fragment, membrane or micelle.

7. The method according to claim 1 wherein the lanthanide is europium, terbium, samarium or dysprosium.

8. The method according to claim 1 wherein two or more bioaffinity assays are carried out using the same sample and assay mixture by labeling the reactants of each assay with a different lanthanide.

9. The method according to claim 8 wherein the fluorescence of the different lanthanides are measured using the same enhancement solution.

* * * * *